United States Patent [19]

Hoehn

[11] 4,282,230

[45] * Aug. 4, 1981

[54] IMIDAZOLYLETHOXY DERIVATIVES OF QUINOLINE-2- OR 4-METHANOLS, ANTIMICROBIAL COMPOSITIONS CONTAINING THEM AND METHOD FOR TREATING BACTERIAL OR FUNGAL INFECTIONS WITH THEM

[75] Inventor: Hans Hoehn, Tegernheim, Fed. Rep. of Germany

[73] Assignee: E. R. Squibb & Sons, Inc., Princeton, N.J.

[ * ] Notice: The portion of the term of this patent subsequent to May 13, 1997, has been disclaimed.

[21] Appl. No.: 94,528

[22] Filed: Nov. 15, 1979

[51] Int. Cl.³ ............... A61K 31/47; C07D 401/12
[52] U.S. Cl. ............... 424/258; 546/153; 546/155; 546/176; 546/177
[58] Field of Search ............... 546/153, 155, 176, 177; 424/258

[56] References Cited

U.S. PATENT DOCUMENTS

| | | | |
|---|---|---|---|
| 3,658,813 | 4/1972 | Godefroi | 260/240 K |
| 3,717,655 | 2/1973 | Godefroi | 260/309 |
| 3,910,925 | 10/1975 | Kreider | 260/288 R |
| 3,991,201 | 11/1976 | Heeres | 424/273 |
| 4,059,705 | 11/1977 | Walker | 424/273 R |
| 4,159,380 | 6/1979 | Hoehn | 546/119 |
| 4,202,985 | 5/1980 | Hoehn | 546/176 |

OTHER PUBLICATIONS

Godefroi et al., "J. Med. Chem.", 1969, vol. 12, 784–791.
Heeres et al., "J. Med. Chem.", 1976, vol. 19 (9), pp. 1148–1155.
Heeres et al., "J. Med. Chem.", 1977, vol. 20 (11), pp. 1111–1120.
Walker, "J. Med. Chem.", 1978, vol. 21 (12), pp. 1335–1338.

*Primary Examiner*—Donald G. Daus
*Assistant Examiner*—Diana G. Rivers
*Attorney, Agent, or Firm*—Lawrence S. Levinson; Burton Rodney

[57] ABSTRACT

Imidazolylethoxy derivatives of quinoline-2- or 4-methanols having the general formula

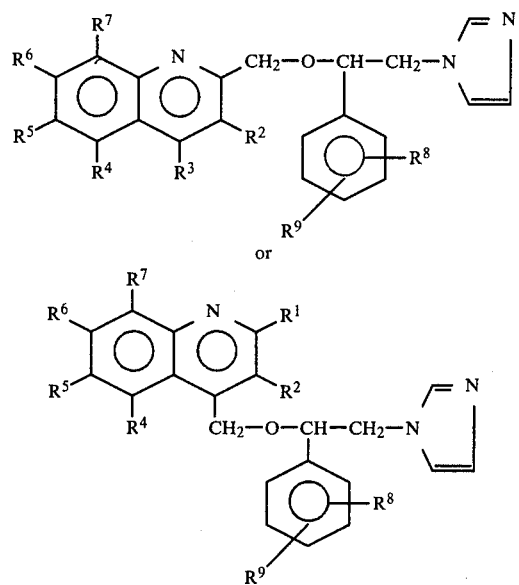

or

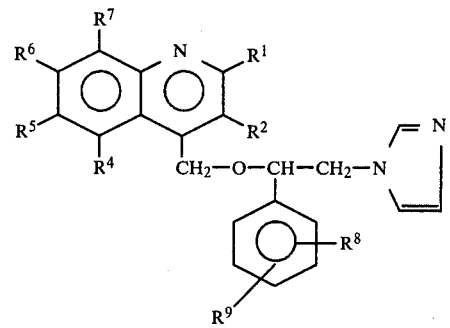

and their acid addition salts are useful as antifungal and antibacterial agents.

20 Claims, No Drawings

IMIDAZOLYLETHOXY DERIVATIVES OF QUINOLINE-2- OR 4-METHANOLS, ANTIMICROBIAL COMPOSITIONS CONTAINING THEM AND METHOD FOR TREATING BACTERIAL OR FUNGAL INFECTIONS WITH THEM

RELATED PENDING APPLICATIONS

U.S. application Ser. No. 954,728, filed Oct. 25, 1978 by H. Hoehn, now U.S. Pat. No. 4,202,985, discloses and claims 2-(1H-imidazol-1-yl)ethoxy derivatives of quinoline-3-methanols and the acid addition salts of these compounds. These new compounds have the general formula

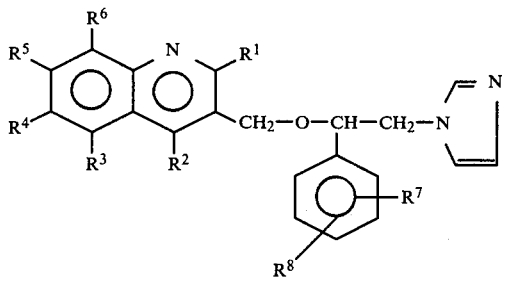

wherein $R^1$ to $R^8$ each is hydrogen, lower alkyl, hydroxy, lower alkoxy, lower alkylthio or halogen.

SUMMARY OF THE INVENTION

This invention relates to new 2-(1H-imidazol-1-yl)ethoxy derivatives of quinoline-2- or 4-methanols and the acid addition salts of these compounds. These new compounds have the general formula

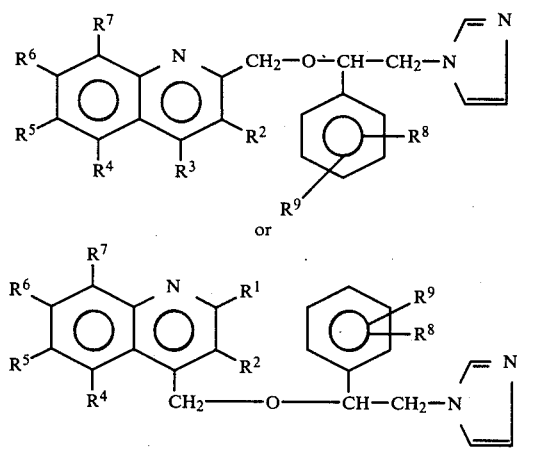

The symbols have the following meaning in formula I and throughout the specification:

$R^1$ to $R^9$ may be the same or different and each may be hydrogen, lower alkyl, hydroxy, lower alkoxy, lower alkylthio or halogen.

The derivatives of the formula I are useful as antimicrobial agents, especially against fungi strains.

DETAILED DESCRIPTION OF THE INVENTION

The lower alkyl groups include straight or branched chain hydrocarbon groups containing 1 to 7 carbon atoms. Examples include methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propylthio, butylthio, isobutylthio, etc. In all of these the $C_1$-$C_4$, especially $C_1$-$C_2$, lower alkyl groups are preferred.

The halogens are the four common halogens, chlorine and bromine being preferred in that order. Preferably, but not necessarily, all halogens in a single compound are the same.

Preferred embodiments of this invention are compounds of formula Ia or Ib wherein $R^1$ is hydroxyl or halogen, $R^5$ is hydrogen or halogen, and $R^3$, $R^4$ and $R^7$ to $R^9$ are hydrogen, lower alkyl of 1 to 4 carbons or halogen.

The most preferred embodiments are compounds of formula Ia wherein $R^2$ to $R^7$ are hydrogen, and $R^8$ and $R^9$ are halogen, particularly chlorine, and compounds of formula Ib wherein $R^1$ is hydroxyl or halogen, particularly chlorine, $R^5$ is hydrogen or halogen, particularly chlorine, $R^2$, $R^4$, $R^6$ and $R^7$ are hydrogen, and $R^8$ and $R^9$ are halogen, particularly chlorine; in each of the preferred formulae Ia and Ib compounds, $R^8$ and $R^9$ are attached in the 2- and 4-positions of the phenyl ring, respectively.

The new compounds of formulae Ia and Ib are formed by reaction of halomethylquinolines of the formula

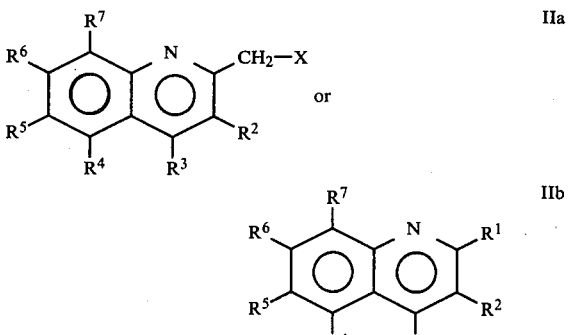

wherein X represents a halogen, preferably chlorine, bromine or iodine, with a substituted 1-(phenyl)-2-(1H-imidazol-1-yl)ethanol of the formula

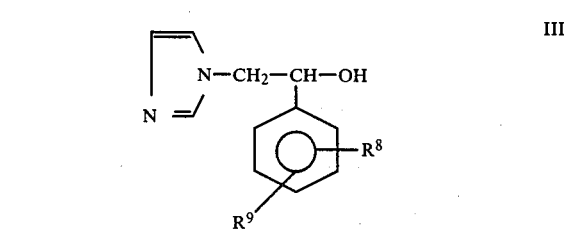

The inorganic acid formed during the reaction is neutralized by a base, e.g., alkali metal hydroxide, carbonate, amine, alcoholate or other similar bases known in the art.

The compounds of formulae IIa and IIb, which are used as starting materials, are produced by the procedures described in Current Science 34, 560 (1965), J. Org. Chem. 26, 4953 (1961) and IL FARMACO-Ed. Sc.—Vol. 34 489 (1979). The compounds of formula III, which are used likewise as starting materials, are produced by the general methods described in J. of Medicinal Chemistry, Vol. 12, 784 (1969).

The compounds of formulae Ia and Ib form salts which are also part of this invention. The salts include acid-addition salts, particularly the non-toxic, physiologically acceptable members. The bases of formulae Ia and Ib form salts by reaction with one or more equivalents of any of a variety of the common inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formulae Ia and Ib. Other salts may then be formed from the free base by reaction with one or more equivalents of acid containing the desired acid group.

The new compounds of formulae Ia and Ib and their salts are useful as anti-fungal and antibacterial agents and may be used to combat infections in various mammalian species, such as mice, rats, dogs, guinea pigs and the like, particularly those due to organisms such as *Candida albicans,* as well as organisms such as *Trichomonas vaginalis* or *Trichophyton mentagrophytes.* For example, a compound or mixture of compounds of formulae Ia and Ib or physiologically acceptable acid addition salts thereof can be administered orally to an infected animal, e.g., to a mouse, in an amount of about 5 to 25 mg per kg per day in 2 to 4 divided doses. These may be conventionally formulated in a tablet, capsule or elixir containing about 10 to 250 mg per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the Celsius scale.

EXAMPLE 1

2-Chloro-4-[[1-(2,4-dichlorophenyl)-2-(1H-imidazol-1-yl)ethoxy]methyl]quinoline

In a three necked flask, fitted with stirrer, reflux condenser and gas inlet tube are introduced 30 g of sodium hydroxide (0.75 mol) and 30 ml of water. While passing nitrogen through the flask, the solution is cooled to 45° C. and then are added 7.7 g of 1-(2,4-dichlorophenyl)-2-(1H-imidazol-1-yl)ethanol (0.03 mol), 0.5 g of benzyltrimethylammonium chloride, 100 ml of tetrahydrofuran and 6.4 g of 2-chloro-4-chloromethylquinoline (0.03 mol). Then the mixture is stirred vigorously for 1.5 hours at 60°-65° C. After cooling the mixture is separated, and the lower aqueous sodium hydroxide is extracted with 20 ml of tetrahydrofuran. The combined tetrahydrofuran layers are dried with sodium sulfate, charcoaled, filtered and after the solvent has been removed, the residual oil is extracted with 175 ml of ether, and the etheral solution is allowed to stand overnight in a refrigerator. The crystallized 2-chloro-4-[[1-(2,4-dichlorophenyl)-2-(1H-imidazol-1-yl)ethoxy]methyl]quinoline is recrystallized from ethyl acetate (refrigerator). Yield 5.5 g (42.3%); m.p. 180°-181° C.

EXAMPLE 2

2,6-Dichloro-4-[[1-(2,4-dichlorophenyl)-2-(1H-imidazol-1-yl)ethoxy]methyl]quinoline, hydrochloride (1:1)

8.7 g of 4-bromomethyl-2,6-dichloroquinoline (0.03 mol), 7.7 g of 1-(2,4-dichlorophenyl)-2-(1H-imidazol-1-yl)ethanol (0.03 mol), 30 g of sodium hydroxide (0.75 mol) dissolved in 30 ml water, 0.5 g of benzyltrimethylammonium chloride and 100 ml of tetrahydrofuran are reacted as described in Example 1. Work up of the mixture results in an oil, which after treatment in boiling ether, is dissolved in 250 ml of ethyl acetate. To the charcoaled solution is added etheral hydrochloric acid. The precipitated hydrochloride is filtered off, washed with ethyl acetate, treated with boiling acetonitrile and finally with anhydrous ether. Yield 4.9 g (32.6%); m.p. 192°-194° C.

A sample recrystallized from ethyl acetate/absolute ethanol (10:1) melts at 193°-194° C.

EXAMPLE 3

6-Chloro-4-[[1-(2,4-dichlorophenyl)-2-(1H-imidazol-1-yl)ethoxy]methyl]-2-quinolinol, hydrochloride (1:1.5)

4.1 g of 4-bromomethyl-6-chloro-2-hydroxyquinoline (0.015 mol), 3.9 g of 1-(2,4-dichlorophenyl)-2-(1H-imidazol-1-yl)ethanol (0.015 mol), 15.2 g of sodium hydroxide (0.38 mol) in 15 ml of water, 0.25 g of benzyltrimethylammonium chloride and 50 ml of tetrahydrofuran are reacted in a manner similar to the procedure of Example 1. After work up of the mixture, the oily product is treated with water and ether. To the aqueous layer is added half concentrated hydrochloric acid (pH 5) and subsequently aqueous ammonia (10%) for neutralization of the hydrochloride. The deposited oily product is extracted with chloroform and the chloroform layer is washed with water, dried and charcoaled. Then the solvent is removed in vacuo, the solid product dissolved in ethyl acetate and to the clear solution is added etheral hydrochloric acid. The precipitated hydrochloride (3.4 g) is washed with ethyl acetate, treated with boiling acetonitrile and then with anhydrous ether. The filtered off product, which contains two moles of crystal water, is dried at 70°-75° C.; m.p. 176°-178° C.

EXAMPLE 4

4-[[1-(2,4-Dichlorophenyl)-2-(1H-imidazol-1-yl)ethoxy]methyl]-2-quinolinol 7.2 g of 4-bromomethyl-2-hydroxyquinoline (0.03 mol), 7.7 g of 1-(2,4-dichlorophenyl)-2-(1H-imidazol-1-yl)ethanol (0.03 mol), 30 g sodium hydroxide (0.75 mol) in 30 ml of water, 0.5 g benzyltrimethylammonium chloride and 45 ml of tetrahydrofuran are reacted in a manner as described in Example 1. After work up of the reaction mixture the sodium salt of the title compound is dissolved in 400 ml of water and acidified with acetic acid. After standing overnight, the solution is filtered and then neutralized with aqueous ammonia. The deposited oil is extracted with chloroform, the chloroform layer washed with water, dried with sodium sulfate and evaporated. The residual oil (8 g) is dissolved in 100 ml of ethyl acetate, charcoaled and allowed to stand overnight in the refrigerator. The crystallized 4-[[1-(2,4-dichlorophenyl)-2-(1H-imidazol-1-yl)ethoxy]methyl]-2-quinolinol melts at 190°–192° C.

EXAMPLE 5

2-[[1-(2,4-Dichlorophenyl)-2-(1H-imidazol-1-yl)ethoxy]methyl]quinoline, hydrochloride (1:2)

3.2 g of 2-Chloromethylquinoline hydrochloride (0.015 mol) (commercially available), 3.85 g of 1-(2,4-dichlorophenyl)-2-(1H-imidazol-1-yl)ethanol (0.015 mol), 14.8 g sodium hydroxide (0.37 mol) in 25 ml of water, 0.25 g of benzyltrimethylammonium chloride and 40 ml of tetrahydrofuran are reacted in a manner as described in Example 1. After work up, the oily product (6.4 g) is dissolved in 150 ml of ether, charcoaled and then etheral hydrochloric acid is added to the clear solution while stirring. The precipitated hydrochloride (5.8 g) is filtered off, washed with ether and hexane and recrystallized from acetonitrile; m.p. 148°–149° C.

The following additional products of formula D or E are obtained by the procedure of Example 1 by reacting the unsubstituted or substituted 1-phenyl-2-(1H-imidazol-1-yl)ethanol of formula A with the unsubstituted or substituted 2-chloromethylquinoline of formula B or the unsubstituted or substituted 4-chloromethylquinoline of formula C. The substituents apply to the respective formulae.

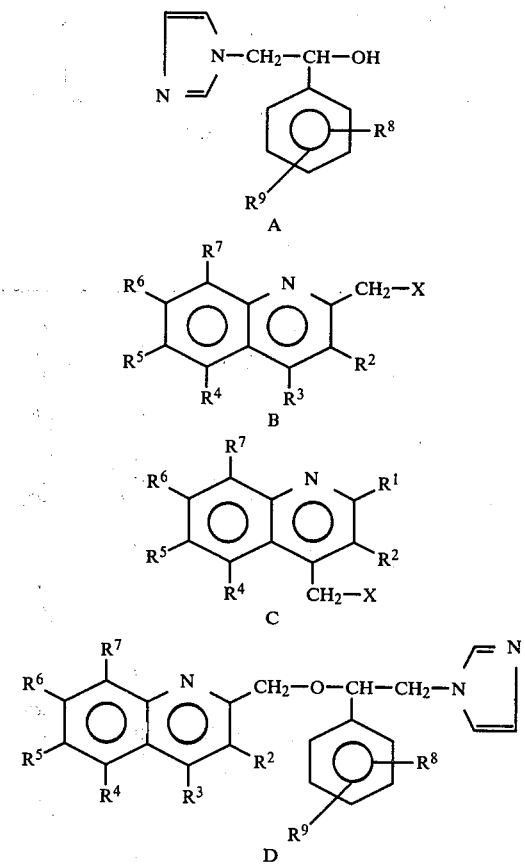

| Ex. No. | $R^2$ | $R^3$ | $R^4$ | $R^5$ | $R^6$ | $R^7$ | $R^8$ | $R^9$ |
|---|---|---|---|---|---|---|---|---|
| 6. | H | H | H | H | H | H | H | H |
| 7. | $CH_3$ | $CH_3$ | —OH | —OH | H | H | H | H |
| 8. | $C_2H_5$ | H | —$CH_3$ | —$OC_2H_5$ | H | H | 2-Cl | 4-Cl |
| 9. | $C_2H_5$ | $C_2H_5$ | $CH_3$ | —$OCH_3$ | H | H | H | 4-Cl |
| 10. | $C_2H_5$ | $CH_3$ | H | Br | H | H | H | 3-Br |
| 11. | $C_2H_5$ | $CH_3$ | H | H | H | H | 2-Br | 4-Br |
| 12. | $C_2H_5$ | H | H | Br | H | H | 3-Br | 4-Br |
| 13. | $C_2H_5$ | H | $CH_3$ | H | —$OCH_3$ | H | H | 4-Cl |
| 14. | $C_2H_5$ | H | $C_2H_5$ | Cl | —OH | H | H | 2-Cl |
| 15. | —OH | $CH_3$ | H | —$OC_2H_5$ | H | —$CH_3$ | 2-$CH_3$ | 4-$CH_3$ |
| 16. | $C_2H_5$ | $C_3H_7$ | H | Cl | H | H | H | 4-$OCH_3$ |
| 17. | $C_2H_5$ | H | $C_6H_5$ | Cl | H | H | H | 2-$OCH_3$ |
| 18. | $C_3H_7$ | H | H | —OH | H | H | H | 3-Cl |
| 19. | H | H | H | Cl | Cl | —OH | 2-Cl | 4-Cl |
| 20. | $CH_3$ | $CH_3$ | H | H | H | H | H | 4-Cl |
| 21. | H | H | H | Cl | H | H | H | H |
| 22. | Cl | H | H | Cl | H | H | 2-Cl | 4-Cl |
| 23. | Cl | $CH_3$ | H | Cl | H | H | 3-Cl | 4-Cl |
| 24. | $C_2H_5$ | —OH | H | Cl | H | H | H | 4-Cl |
| 25. | $C_2H_5$ | $CH_3$ | H | H | H | Cl | 2-Cl | 4-Cl |
| 26. | H | —$SCH_3$ | H | Cl | $C_2H_5$ | H | H | 4-Cl |

-continued

| Ex. No. | R¹ | R² | R³ | R⁴ | R⁵ | R⁶ | R⁷ | E |
|---|---|---|---|---|---|---|---|---|
| 27. | H | CH₃ | H | Cl | H | CH₃ | H | 4-Cl |
| 28. | —OC₂H₅ | CH₃ | H | Br | H | H | H | 4-Cl |
| 29. | —SC₂H₅ | H | H | Cl | H | H | 2-Cl | 4-Cl |
| 30. | C₂H₅ | H | —SCH₃ | H | H | H | H | 4-Br |
| 31. | H | H | H | —SCH₃ | H | H | 2-Cl | 4-Cl |
| 32. | —OC₂H₅ | CH₃ | H | Cl | H | H | H | 4-Cl |
| 33. | CH₃ | H | H | —SCH₃ | H | H | H | 4-SCH₃ |
| 34. | C₂H₅ | H | H | I | H | H | H | 4-Cl |
| 35. | C₂H₅ | H | H | —OH | H | H | 3-OH | 5-OH |
| 36. | C₂H₅ | CH₃ | H | —OC₄H₉ | H | H | H | 4-Cl |
| 37. | H | H | H | —OC₃H₇ | H | H | 2-Cl | 4-Cl |
| 38. | C₂H₅ | H | H | H | H | —SCH₃ | 2-Cl | 4-Cl |
| 39. | C₂H₅ | H | CH₃ | Cl | CH₃ | —OH | H | 4-Cl |

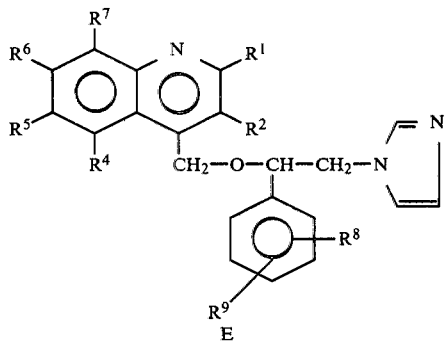

| Ex. No. | R¹ | R² | R⁴ | R⁵ | R⁶ | R⁷ | R⁸ | R⁹ |
|---|---|---|---|---|---|---|---|---|
| 40. | H | H | H | H | H | H | H | H |
| 41. | CH₃ | CH₃ | —OH | —OH | H | H | H | H |
| 42. | C₂H₅ | H | —CH₃ | —OC₂H₅ | H | H | 2-Cl | 4-Cl |
| 43. | C₂H₅ | C₂H₅ | CH₃ | —OCH₃ | H | H | H | 4-Cl |
| 44. | C₂H₅ | CH₃ | H | Br | H | H | H | 3-Br |
| 45. | C₂H₅ | CH₃ | H | H | H | H | 2-Br | 4-Br |
| 46. | C₂H₅ | H | H | Br | H | H | 3-Br | 4-Br |
| 47. | C₂H₅ | H | CH₃ | H | —OCH₃ | H | H | 4-Cl |
| 48. | C₂H₅ | H | C₂H₅ | Cl | —OH | H | H | 2-Cl |
| 49. | —OH | CH₃ | H | —OC₂H₅ | H | —CH₃ | 2-CH₃ | 4-CH₃ |
| 50. | C₂H₅ | C₃H₇ | H | Cl | H | H | H | 4-OCH₃ |
| 51. | C₂H₅ | H | C₆H₅ | Cl | H | H | H | 2-OCH₃ |
| 52. | C₃H₇ | H | H | —OH | H | H | H | 3-Cl |
| 53. | H | H | H | Cl | Cl | —OH | 2-Cl | 4-Cl |
| 54. | CH₃ | CH₃ | H | H | H | H | H | 4-Cl |
| 55. | H | H | H | Cl | H | H | H | H |
| 56. | Cl | H | H | Cl | H | H | 2-Cl | 4-Cl |
| 57. | Cl | CH₃ | H | Cl | H | H | 3-Cl | 4-Cl |
| 58. | C₂H₅ | —OH | H | Cl | H | H | H | 4-Cl |
| 59. | C₂H₅ | CH₃ | H | H | H | Cl | 2-Cl | 4-Cl |
| 60. | H | —SCH₃ | H | Cl | C₂H₅ | H | H | 4-Cl |
| 61. | H | CH₃ | H | Cl | H | CH₃ | H | 4-Cl |
| 62. | —OC₂H₅ | CH₃ | H | Br | H | H | H | 4-Cl |
| 63. | —SC₂H₅ | H | H | Cl | H | H | 2-Cl | 4-Cl |
| 64. | C₂H₅ | H | —SCH₃ | H | H | H | H | 4-Br |
| 65. | H | H | H | —SCH₃ | H | H | 2-Cl | 4-Cl |
| 66. | —OC₂H₅ | CH₃ | H | Cl | H | H | H | 4-Cl |
| 67. | CH₃ | H | H | —SCH₃ | H | H | H | 4-SCH₃ |
| 68. | C₂H₅ | H | H | I | H | H | H | 4-Cl |
| 69. | C₂H₅ | H | H | —OH | H | H | 3-OH | 5-OH |
| 70. | C₂H₅ | CH₃ | H | —OC₄H₉ | H | H | H | 4-Cl |
| 71. | H | H | H | —OC₃H₇ | H | H | 2-Cl | 4-Cl |
| 72. | C₂H₅ | H | H | H | H | —SCH₃ | 2-Cl | 4-Cl |
| 73. | C₂H₅ | H | CH₃ | Cl | CH₃ | —OH | H | 4-Cl |

What is claimed is:
1. A compound of the formula

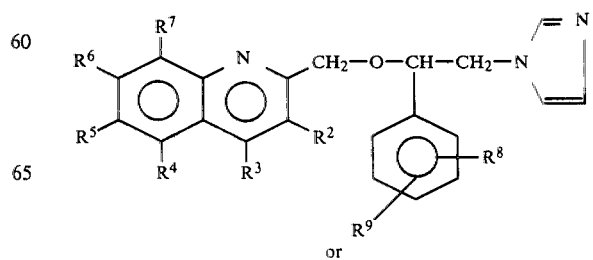

or

-continued

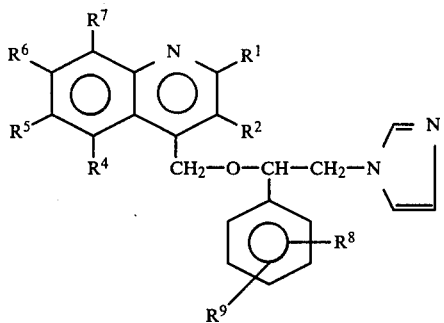

wherein $R^1$ to $R^9$ each is hydrogen, hydroxy, halogen, lower alkyl containing 1 to 7 carbons, lower alkoxy containing 1 to 7 carbons, or lower alkylthio containing 1 to 7 carbons, and physiologically acceptable acid addition salts thereof.

2. A compound as defined in claim 1 wherein $R^1$ where present is hydroxy or halo.

3. A compound as defined in claim 1 wherein $R^5$ is halo or hydrogen.

4. A compound as in claim 1 wherein $R^8$ and $R^9$ each is halo.

5. A compound as defined in claim 1 wherein $R^8$ is 2-chloro and $R^9$ is 4-chloro.

6. A compound as defined in claim 1 wherein $R^1$ to $R^9$ where present each is hydrogen or halogen.

7. A compound as defined in claim 1 having the formula

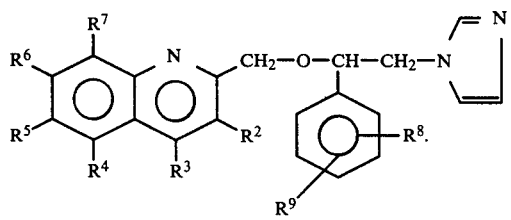

8. A compound as defined in claim 7 wherein $R^2$, $R^3$, $R^4$, $R^5$, $R^6$ and $R^7$ each is hydrogen; and $R^8$ and $R^9$ each is halogen; and hydrohalide salts thereof.

9. A compound as defined in claim 8 wherein $R^8$ is 2-chloro and $R^9$ is 4-chloro; and hydrochloride salts thereof.

10. A compound as defined in claim 1 having the formula

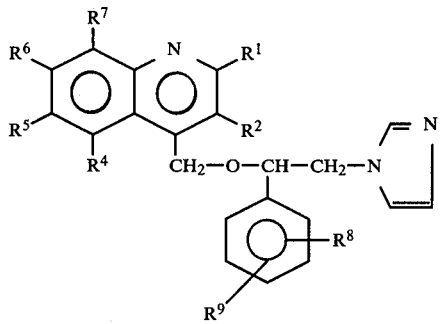

11. A compound as defined in claim 10 wherein $R^1$ is hydroxyl; $R^2$, $R^4$ to $R^7$ each is hydrogen; and $R^8$ and $R^9$ each is halogen.

12. A compound as defined in claim 11 wherein $R^8$ is 2-chloro and $R^9$ is 4-chloro.

13. A compound as defined in claim 11 wherein $R^1$ is halogen; $R^2$, $R^4$ to $R^7$ each is hydrogen; and $R^8$ and $R^9$ each is halogen.

14. A compound as defined in claim 13 wherein $R^1$ is chloro, $R^8$ is 2-chloro, and $R^9$ is 4-chloro.

15. A compound as defined in claim 10 wherein $R^1$ is hydroxyl; $R^5$ is halogen; $R^2$, $R^4$, $R^6$, and $R^7$ are each hydrogen and $R^8$ and $R^9$ are each halogen; and hydrohalide salts thereof.

16. A compound as defined in claim 15 wherein $R^5$ is chloro; $R^8$ is 2-chloro and $R^9$ is 4-chloro; and hydrochloride salts thereof.

17. A compound as defined in claim 10 wherein $R^1$ and $R^5$ each is halogen, $R^2$, $R^4$, $R^6$ and $R^7$ each is hydrogen; and $R^8$ and $R^9$ each is halogen, and hydrohalide salts thereof.

18. A compound as in claim 17 wherein $R^1$ and $R^5$ each is chloro; $R^8$ is 2-chloro; and $R^9$ is 4-chloro, and hydrochloride salts thereof.

19. An antimicrobial composition comprising a compound as defined in claim 1 and a pharmaceutically acceptable carrier therefor.

20. A method for treating bacterial or fungal infections in mammals which comprises administering to a mammalian host an effective amount of a compound as defined in claim 1.

* * * * *